(12) United States Patent
Falo, Jr. et al.

(10) Patent No.: US 7,176,186 B1
(45) Date of Patent: Feb. 13, 2007

(54) STIMULATION OF CELL-MEDIATED IMMUNE RESPONSES BY TARGETED PARTICULATE GENETIC IMMUNIZATION

(75) Inventors: Louis D. Falo, Jr., Pittsburgh, PA (US); Kenneth L. Rock, Chestnut Hill, MA (US)

(73) Assignees: The University of Pittsburgh of the Commonwealth System of Higher Education, Pittsburgh, PA (US); Dana-Farber Cancer Institute, Boston, MA (US)

( * ) Notice: Subject to any disclaimer, the term of this patent is extended or adjusted under 35 U.S.C. 154(b) by 1147 days.

(21) Appl. No.: 08/931,219

(22) Filed: Sep. 16, 1997

(51) Int. Cl.
- *A61K 48/00* (2006.01)
- *A61K 35/00* (2006.01)
- *C12N 15/09* (2006.01)
- *C12N 15/85* (2006.01)

(52) U.S. Cl. .................. 514/44; 424/93.1; 424/93.2; 424/93.21; 435/455; 435/459; 435/470

(58) Field of Classification Search .................. 514/44; 435/320.1, 172.3, 69.1, 69.3, 455, 459, 470; 424/93.21, 93.1, 93.2
See application file for complete search history.

(56) References Cited

U.S. PATENT DOCUMENTS 5,593,972 A * 1/1997 Weiner et al. ................. 514/44
2002/0054864 A1* 5/2002 Falo et al.

OTHER PUBLICATIONS

Schofield and Caskey, British Medical Bulletin, vol. 51, pp. 56-71, 1995.*
Marshall, Science, vol. 269, pp. 1050-1055, Aug. 25, 1995.*
Coghlan, Focus, vol. 145, pp. 14-15, Nov. 25, 1995.*
Brown, The Washington Post, Dec. 8, 1995.*
Bignon et al., European Journal of Dermatology, vol. 6, pp. 159-163, 1996.*
Cournoyer and Caskey, Annu. Rev. Immunol., vol. 11, pp. 297-329, 1993.*
Hanania et al., American Journal of Medicine, vol. 99, pp. 537-552, Nov. 1995.*
Orkin and Motulsky, Report and Recommendation of the Panel . . . Gene Therapy, Dec. 7, 1995.*
Nabel et al., Human Gene Therapy, vol. 3, pp. 399-410, 1992.*
Eisenbraun et al., DNA Cell Biol., vol. 12, pp. 791-797, 1993.*
Robinson et al., Vaccine, vol. 11, pp. 957-960, 1993.*
Nakano et al., Journal of Virology, vol. 71, pp. 7101-7109, Sep. 1997.*
Culver et al., British Medical Bulletin, vol. 5, pp. 192-204, Jan. 1995.*
Barry et al., Vaccine, vol. 15, pp. 788-791, 1997.*
Tang et al., Nature, vol. 356, pp. 152-154, Mar. 12, 1992.*
Barry et al., Biotechniques, vol. 16, pp. 616-618, Apr. 1994.*
Hui et al., Journal of Immunological Methods, vol. 171, pp. 147-155, May 16, 1994.*
Whalen et al., Clinical Immunology and Immunopathology, vol. 75, pp. 1-12, Apr. 1995.*
Boon et al., Annual Review of Immunology, vol. 12, pp. 337-365, 1994.*
Kawakami et al., Journal of Immunology, vol. 154, pp. 3961-3968, Apr. 15, 1995.*
Frey et al., Clinical Immunology and Immunopathology, vol. 69, pp. 223-233, Nov. 1993.*
Appleman et al., International Journal of Cancer, vol. 61, pp. 887-894, Jun. 9, 1995.*
Johnston et al., Methods in Cell Biology, vol. 43, pp. 353-365, 1994.*
Klein et al., Current Opinion in Biotechnology, vol. 4, pp. 583-590, Oct. 1993.*
Fundamental Immunology, William E. Paul, Raven Press: New York, Third Edition, pp. 121 & 593, 1993.*
Miller (1995, FASEB J., vol. 9, pp. 190-199).*
Deonarain (1998, Expert Opin. Ther. Pat., vol. 8, p. 53-69).*
Verma (Sep. 1997, Nature, vol. 389, pp. 239-242).*
Crystal (1995, Science, vol. 270, p. 404-410).*
Stricker (Medical Hypotheses, Jun. 1997, vol. 48, pp. 527-529).*
Bangham, Nov. 29, 1997, Lancet, vol. 350, pp. 1617-1621.*
Veljkovic (Vaccine, 2001, vol. 19, p. 1855-1862).*
McMichael, Annual Rev. Immunol., 1997, vol. 15, p. 271-296.*
Weber (Eur. J. Clin. Microbiol. Infect. Dis., Nov. 2001, vol. 20, p. 800-803).*
Webster (Vaccine, Dec. 1994, vol. 12, No. 16, p. 1495-1498).*
Robinson (Seminars in Immunology, 1997, vol. 9, p. 271-283).*
Kuby (Immunology, 1992, W.H. Freeman and Company, New York, p. 208).*
Peachman (Methods, 2003, vol. 31, p. 232-242).*
Haynes (AIDS research and human retroviruses, 1994, vol. 10, Supplement 2, p. S43-45).*
Haynes (Vaccine, 1994, Cold Spring Harbor, Modern approaches to new vaccines including prevention of AIDS, p. 65-70).*
Lai (DNA and cell biology, Jul. 1995, vol. 14, No. 7, p. 643-651).*
Hui (J. Immunological Methods, May 16, 1994, vol. 171, p. 147-155).*

(Continued)

*Primary Examiner*—Michael Wilson
(74) *Attorney, Agent, or Firm*—Foley & Lardner LLP (57) ABSTRACT

The present invention relates to various methods of genetic immunization for the purpose of providing antigen-specific immunity in a mammalian host, including a human host. The invention is based on the ability to direct particulate polynucleotides which express an antigenic protein or protein fragment to the cytoplasm of host target cells, such as antigen presenting cells. A directed delivery of such particulate polynucleotides to the cytoplasm of antigen presenting cells will stimulate antigen-specific CTL production, thus promoting destruction of affected cells such as neoplastic cells and virally infected cells.

79 Claims, 6 Drawing Sheets

OTHER PUBLICATIONS

Johnston (Methods in cell Biology, 1994, vol. 43, Chapt, 14, p. 353-365).*
Shiver (Advanced Drug Delivery Rev., 1996, vol. 21, p. 19-31).*
Larregina (Gene Therapy, 2001, vol. 8, p. 608-617).*
Tuting (J. Invest. Dermatol., 1998, vol. 111, p. 183-188).*
Dorlands Medical Dictionary page showing the cross section of the skin.*
Dorlands Medical Dictionary definition of Langerhans cells.*
Barry (1994, BioTechniques, vol. 16, No. 4, p. 616-618).*
Fuller (AIDS Research and Human Retroviruses, Nov. 1994, vol. 10, No. 11, p. 1433-1441).*

* cited by examiner

STIMULATION OF CELL-MEDIATED IMMUNE RESPONSES BY TARGETED PARTICULATE GENETIC IMMUNIZATION

1. INTRODUCTION

Genetic immunization for the purpose of stimulating antigen-specific immunity in a mammalian host, including a human host, is at the core of the present disclosure. This specification discloses delivery of particulate polynucleotides to the cytoplasm of host target cells, such as antigen presenting cells. These particulate polynucleotides encode an antigenic protein or antigenic protein fragment which accesses the cytoplasm of the target cell. Expression of the antigen gene results in antigen-specific immune responses, including but not limited to, the induction of antigen-specific cytotoxic T-lymphocytes (CTLs). Cytosolic access of the antigen allows membrane presentation of the antigenic peptide through the endogenous MHC class I pathway. Membrane presentation via the endogenous MHC class I pathway stimulates the induction of antigen-specific CTLs. Induced antigen-specific CTLs then target and destroy antigen-expressing affected host cells such as neoplastic cells or virally infected cells.

2. BACKGROUND OF THE INVENTION

Cytotoxic T-lymphocytes (CTLs) are a critical component of effective human immune responses to tumors or viral infections. Cytotoxic T-lymphocytes destroy neoplastic cells or virus infected cells through recognition of antigenic peptides presented by MHC class I molecules on the surface of the affected target cells. These antigenic peptides are degradation products of foreign proteins present in the cytosol of the affected cell, which are processed and presented to CTLs through the endogenous MHC class I processing pathway.

Although the recognition of a foreign protein in the context of the MHC class I molecule may be sufficient for the recognition and destruction of affected target cells by CTLS, the induction of antigen-specific CTLs from T-lymphocyte precursors requires additional signals. Specialized antigen presenting cells (APCs) can provide both the antigen-MHC class I ligand and the accessory signals required in the induction phase of CTL-mediated immunity. General properties of APCs include MHC class I and class II expression, expression of various adhesion molecules important for APC-lymphocyte interaction, and expression of costimulatory molecules such as CD80 and CD86. Examples of APCs include macrophages and dendritic cells (including cutaneous epidermal Langerhans cells, dermal dendritic cells, and dendritic cells resident in lymph nodes and spleen).

Attempts to induce antigen-specific CTL responses in vivo by immunization with killed tumor cells, killed virus-infected cells, or component proteins have generally been unsuccessful, presumably because proteins in the extracellular fluids cannot enter the cytosol and access the MHC class I presentation pathway.

Genetic immunization possess several attractive features. Several in vivo gene transfer methods result in transgene expression, including retroviral or adenoviral mediated gene transfer, and direct injection of naked DNA (for a review, see Krishnaw, et al., 1995, *Nature Med.* 1: 521–522 and Pardoll, et al., 1995, *Immunity* 3:165–169.)

Williams, et al. (1991, *Proc. Natl. Acad. Sci. USA* 88: 2726–2730) showed the expression of the protein luciferase in intact epidermal cells following biolistic (biobalistic) delivery of the firefly luciferase gene. CTL responses were not addressed in these studies, nor were specific host cells targeted to generate cell-mediated immune responses.

Tang, et al. (1992, *Nature* 356: 152–154) utilized a biolistic (biobalistic) device to produce a humoral response to a foreign protein. A gene encoding hGH under control of either the CMV promoter or the β-actin promoter was delivered to the epidermal tissue of mice. Anti-hGH antibodies were detected in mice in response to this immunization procedure. Tang, et al. does not disclose genetic immunization targeting the cell-mediated immune pathway. Direct targeting of APC cells for genetic immunization is not disclosed or suggested by Tang, et al.

Fynan, et al. (1993, *Proc. Natl. Acad. Sci. USA* 90: 11478–11482) confirmed the findings of Tang, et al. by using a plasmid DNA construct encoding an influenza virus hemagglutinin glycoprotein. Fynan, et al. compared humoral responses generated by gene gun delivery of DNA coated gold beads to the epidermis with other mechanisms and found that the use of a biolistic (biobalistic) device 1) resulted in 95% protection to a lethal influenza challenge, 2) was the most efficient route for DNA immunization, proving to be substantially more effective than mucosal, intramuscular, or intravenous administration, and, 3) required 250 to 2500 times less DNA than saline inoculations. Direct targeting of APC cells for genetic immunization is not disclosed or suggested by Fynan, et al. CTL-mediated immunity is not addressed.

Liu and colleagues (Montgomery et al., 1993, *DNA Cell Biol.* 12:777–783; Ulmer et al., 1993, *Science.* 259:1745–1749; Donnelly et al., 1995, *Nature Medicine* 1:583–587.) have demonstrated that untargeted, nonspecific intramuscular injection of naked DNA induces antigen-specific CTL responses to viral proteins and protective immunity to viral challenge. The studies do not disclose targeting of genetic material to APCs for genetic immunization.

Sun, et al. (1995, *Proc. Natl. Acad. Sci. USA* 92: 2889–2893) utilized a biolistic (biobalistic) device to produce an anti-tumor response in mice. The authors delivered a plasmid construct expressing IL-6 directly to a tumor site in mice. Expression of IL-6 afforded a form of cytokine gene therapy nonspecifically directed at the tumor. Antigen-specific immunity to tumors was not claimed. Direct targeting of APC cells for genetic immunization is not disclosed or suggested by Sun, et al.

Kundig et al. (1995, *Science.* 268:1343–1346) demonstrate that protein antigen localization to the lymphoid organs is critical for the induction of antigen-specific CTL responses in vivo. Genetic immunization is not addressed.

Kovacsovics-Bankowski and Rock (1995, *Science* 267: 243–246) demonstrate a phagosome-to-cytosol pathway for protein antigens not normally presented through the MHC class I endogenous pathway. The authors speculate that proteins in particulate form internalized within phagosomes are in fact able to enter the cytosolic pathway for MHC class I presentation. The capacity of functionally intact genetic material to enter the cytosol through a phagosome-to-cytosol pathway is not addressed.

Falo, et al. (1995, *Nature Med.* 1: 649–653) offer in vivo support for phagosome-to-cytosol pathway by showing that delivery of particulate protein antigen directly into animals results in antigen-specific CTL mediated tumor immunity in mice. They demonstrate that proteins injected directly into animals in vivo can specifically enter the phagosome-cytosol pathway of APCs if administered in particulate form. No details are forwarded regarding genetic immunization procedures. The capacity of in vivo administered genetic material to enter the cytosol of APCs, or other cell types, functionally intact through this pathway is not addressed.

Pardoll and Beckerleg (1995, *Immunity* 3:165–169) have recently reviewed the immunology of naked DNA vaccines. They emphasize the importance of additional studies to define the currently unknown mechanism of DNA immunization. Specifically, they conclude that "it will be important to dissect the mechanisms by which it (naked DNA) activates immune responses. It is only through these studies that intelligent modifications can be introduced to maximize both qualitatively and quantitatively its ultimate potency."

Despite the efforts documented in the above reference material, there remains a need to develop a genetic immunization protocol which specifically targets cell types within the host to stimulate antigen-specific CTL mediated immunity and in turn promote direct destruction of specific neoplastic or virally infected cells within the host. The present invention both addresses and meets this need.

3. SUMMARY OF THE INVENTION

The present invention relates to therapeutic or prophylactic genetic immunization of a mammalian host which comprises delivery of a DNA fragment which encodes an antigenic protein to a target cell within the mammalian host, expression of the recombinant DNA fragment within the host cell, and subsequent presentation of the antigenic peptide or peptides by the host cell so as to stimulate cell-mediated immunity, humoral immunity, or both.

The present invention further relates to therapeutic or prophylactic genetic immunization of a mammalian host which comprises delivery of a DNA sequence encoding an antigenic protein or biologically active fragment thereof to a specific target cell within the mammalian host. Antigenic peptides expressed from the DNA fragment are specific to an affected cell and subsequently stimulate antigen specific CTL production, thereby promoting destruction of affected cells such as neoplastic cells and virally infected cells.

The present invention also relates to genetic immunization with particulate polynucleotides and inoculation of a mammalian host and subsequent delivery of these particulate-based transgenic polynucleotides to the cytosol of the target cell. Once within the confines of the target cell, the particulate polynucleotide expresses a protein or biologically active fragment thereof whereby an appropriate antigenic peptide fragment is generated and presented to the target cell membrane via the endogenous MHC class I pathway. Proper presentation of the antigenic peptide or peptides of interest through the MHC class I pathway stimulates CTL production and in turn promotes destruction of cells such as neoplastic cells or virally infected cells.

Therefore, the present invention also relates to in vivo methods of therapeutic or prophylactic genetic immunization of a mammalian host which comprises generating a DNA fragment which expresses an antigenic protein or antigenic protein fragment, distributing the DNA fragment on a particle surface which results in a particulate polynucleotide, inoculating the mammalian host with said particulate polynucleotide and delivering the particulate polynucleotide to the cytoplasm of a target cell of the mammalian host so that the expressed antigenic protein or antigenic protein fragment is presented to the membrane surface of said target cell through the MHC class I pathway.

In the present invention it is preferable that the mammalian host be a human.

It is also preferable in the various embodiments disclosed within this specification that the DNA fragment of interest express 1) a tumor rejection antigen or an antigenic protein fragment or 2) a viral antigen or an antigenic protein fragment. Examples of human TRAs which may be utilized in the present invention include but are not limited to MAGE-1, MAGE 3, Melan-A, gp100, p53, CEA and HER2/neu. Examples of viral antigens which may be utilized in the present invention include but are not limited to HIV gp120, HIV gp160, Influenza virus nucleoprotein and Hepatitis B surface antigen.

The preferred target cell in the present invention is an APC while the preferred localization or migration of the APC target cell is the lymphoid tissue of the human host.

In one embodiment of the present invention the mammalian host is immunized with the particulate polynucleotide by utilizing a microprojectile bombardment device. Specifically, a mammalian host is immunized by inoculation with a particulate polynucleotide by a biolistic (biobalistic) procedure such that the particulate polynucleotide enters the cytoplasm of at least an appropriate number of host cells. The transgenic polynucleotide is expressed at biologically effective levels such that antigenic peptide fragments are presented to the endogenous MHC class I pathway and displayed on the membrane surface of the host cells. Endogenous host cell membrane presentation of the introduced antigen promotes induction of antigen-specific CTLs, which in turn circulate throughout the mammalian host, preferably a human host, to destroy neoplastic cells or virally infected cells.

In a specific embodiment of the present invention a mammalian host, preferably a human, is immunized with a particulate polynucleotide by microprojectile bombardment inoculation such that the particulate polynucleotide enters the cytoplasm of at least an appropriate number of host cells, including APCs, in the path of the projectiles as a direct result of non-specific projectile bombardment. When the skin is bombarded, APCs of the skin which may be bombarded include, but are not limited to epidermal Langerhans cells, keratinocytes, or dermal dendritic cells. When the lymphoid tissue is bombarded, APCs of the lymphoid tissue which may be bombarded include, but are not limited to resident dendritic cells, macrophages, stromal cells, T-lymphocytes, or β-lymphocytes.

In another embodiment of the present invention a mammalian host is immunized with a particulate polynucleotide by direct injection, including but not limited to subcutaneous injection, epidermal injection, dermal injection, lymphatic injection and intra venous injection. The particulate polynucleotide enters host cells and is expressed at biologically effective levels such that antigenic peptide fragments are presented to the endogenous MHC class I pathway and displayed on the membrane surface of the host cell. Endogenous target cell membrane presentation promotes induction of antigen-specific CTLs, which in turn circulate throughout the mammalian host, preferably a human host, to destroy neoplastic cells or virally infected cells.

In an especially preferred embodiment the particulate polynucleotide is delivered to a human host by subcutaneous injection and targeted to APCs through a phagosome-to-cytosol pathway and expressed at biologically effective levels by APCs. The present invention discloses that direct injection of the particulate polynucleotide complex via a subcutaneous inoculation route results in targeted delivery to APCs and antigen expression in the lymphoid tissue.

In another especially preferred embodiment of the present invention, subcutaneous injection for direct targeting to an APC involves delivery of a particulate polynucleotide encoding a tumor rejection antigen (TRA) or biologically active fragment thereof. Directed delivery of a TRA particulate polynucleotide in this manner will maximize entry of tumor specific antigenic peptides into the class I pathway as well as avoiding substantial particulate translocation within non-APC cells.

In another especially preferred embodiment of the present invention, subcutaneous injection for direct targeting to an APC involves delivery of a particulate polynucleotide encoding a viral antigen or biologically active fragment thereof. Directed delivery of a viral antigen encoding particulate polynucleotide in this manner will maximize entry of viral specific antigenic peptides into the class I pathway as well as avoiding substantial particulate translocation within non-APC cells.

It will also be known to the skilled artisan that particulates composed of a variety of materials including but not limited to gold, iron, and synthetic plastics can access the phagosome-to-cytosol pathway used to target APCs in this invention.

In another embodiment of the present invention a mammalian host is immunized by injection, including but not limited to subcutaneous injection, epidermal injection, dermal injection, lymphatic injection and intra venous injection, with syngeneic APCs that have been antigen loaded in vitro by co-incubation with particulate polynucleotide. Particulate polynucleotides may, for example, enter the APC in vitro by either microprojectile bombardment or the phagosome-to-cytosol pathway. Specifically, a mammalian host is immunized with particulate polynucleotide transfected APCs, such that the particulate polynucleotide specifically enters APCs in vitro and the APCs are injected into the host. Subsequent to uptake by APCs, the transgenic polynucleotide is expressed at biologically effective levels such that antigenic peptide fragments are processed and presented through the endogenous MHC class I pathway and displayed on the membrane surface of the APCs. After injection of such APCs, endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy neoplastic cells or virally infected cells.

In another embodiment of the present invention a mammalian host is immunized by injection, including but not limited to subcutaneous injection, epidermal injection, dermal injection, lymphatic injection and intra venous injection, with syngeneic APCs that have been transfected in vitro with particulate polynucleotides. Specifically, a mammalian host is immunized with particulate polynucleotide transfected APCs, such that the particulate polynucleotide enters APCs in vitro and the APCs are then injected into the host. Particulate polynucleotides may, for example, enter the APC in vitro by either microprojectile bombardment or the phagosome-to-cytosol pathway. APCs are transfected in vitro with antigen encoding polynucleotide and/or polynucleotides encoding a molecule or molecules which increases the efficiency of the antigen presenting function of the APC. Such molecules include but are not limited to cytokines and costimulatory molecules. Examples of cytokines include but are not limited to IL-12, IL-2, and IL-4. Examples of costimulatory molecules include but are not limited to CD80 and CD86. Subsequent to entry into APCs, the transgenic antigen encoding polynucleotide is expressed at biologically effective levels such that antigenic peptide fragments are processed and presented through the endogenous MHC class I pathway and displayed on the membrane surface of the APCs. After injection of such APCs, endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy neoplastic cells or virally infected cells. Subsequent to entry into APCs, the transgenic cytokine and/or costimulatory encoding polynucleotide is expressed at biologically effective levels such that the antigen presenting function of the APC results in the induction of antigen specific immune responses either at the site of the injection, or in the lymphoid tissue.

It will also be known to the skilled artisan that polynucleotides can be precipitated onto particulates composed of a variety of materials including but not limited to gold, iron, and synthetic plastics.

It will also be known to the skilled artisan that various recombinant vectors may be used to generated the transgene sequence to be applied in particulate form. The preferred vector, due primarily to ease of handling, is a DNA plasmid vector.

It will be known to the skilled artisan that APCs can be obtained from a variety of host tissue including, but not limited to bone marrow and peripheral blood, and that said APCs can be manipulated in vitro and then reintroduced into said host.

It is an object of the present invention to provide therapeutic or prophylactic genetic immunization against neoplastic cells.

It is another object of the present invention to provide therapeutic or prophylactic genetic immunization against viral infections.

It is an object of the present invention to provide for genetic immunization of a mammalian host, preferably a human, by targeting particulate polynucleotides encoding tumor rejection antigen genes to host immune cells involved in generating a CTL response.

It is an object of the present invention to provide for genetic immunization of a mammalian host, preferably a human, by targeting particulate polynucleotides encoding tumor rejection antigen genes to host antigen presenting cells localized within or capable of trafficking to host lymphoid tissue so as to generate a CTL response.

It is an object of the present invention to provide for genetic immunization of a mammalian host, preferably a human, by targeting particulate polynucleotides encoding viral genes to host immune cells involved in generating a CTL response against the specific viral infection.

It is an object of the present invention to provide for genetic immunization of a mammalian host, preferably a human, by targeting particulate polynucleotides encoding viral genes to host antigen presenting cells localized within host lymphoid tissue so as to generate a CTL response.

4. BRIEF DESCRIPTION OF THE FIGURES

FIG. 1 shows functional presentation of ovalbumin by the transfected tumor cell lines MO4 and EG7. Microcultures were prepared with the T-cell hybridoma RF33.70 (anti-OVA+$K^b$) and the indicated number of transfected (squares) or untransfected (circles) tumor cells in the presence (open symbols) or absence (closed symbols) of added exogenous OVA-peptide SIINFEKL (SEQ ID NO: 1) (10 ng/ml) as described (Rock, et al., 1990, *J. Immunol.* 45:804–811). After 18 hrs incubation, supernatants were harvested and assayed for IL-2 using the indicator cell line HT2 (Rock, et al., 1990, *J. Immunol.* 145: 804–811). (A) B16 and the OVA-transfected subclone MO4. (B)-EL4 and the OVA transfected EL4 subclone EG7. OVA presentation by the OVA-transfected tumors was not significantly enhanced by the presence of exogenous SIINFEKL (SEQ ID NO: 1) in the assay cultures.

FIG. 3 shows that immunization by cutaneous delivery of OVA encoding DNA induces OVA-specific CTLs and antigen-specific, CTL mediated protection from lethal challenge with the OVA expressing melanoma MO4. In vitro restimulated splenocytes from OVA-immunized (genetically immunized as described in Example Section 7) mice were assayed for cytolytic function against the OVA-transfected lymphoma EG7 (closed squares) or the untransfected parent EL4 (open triangles) (A). Effector populations were incubated with complement alone (open squares) or with mAbs against $CD4^+$ (closed triangles), $CD8^+$ (open circles), or $Thy1.2^+$ (closed circles) lymphocytes and complement, then assayed for cytolytic activity against EG7 targets (B). In C–F, mice were genetically immunized with OVA (closed squares) or lacZ (open squares) and boosted 7 days later. Groups of immunized mice were challenged 7 days after the final immunization (day 0) with either the B16 melanoma (D), or the OVA-expressing subclone MO4 (C). Alternatively, immunized mice were divided into 2 groups, one of which was depleted of $CD8^+$ lymphocytes by i.p. injection of anti-CD8 mAb 7 and 9 days after the last immunization. Intact (E) and $CD8^+$ depleted (F) mice were then challenged 10 days after the final immunization (day 0) with MO4. Survival was reported as the percentage of surviving animals (C–F). Animals surviving on day 60 had no sign of tumor growth. All experiments included 5 mice per group and were repeated at least 3 times. Mice that became moribund were sacrificed according to animal care guidelines.

FIG. 4 shows that antigen presenting cells internalize and express particulate polynucleotides, and process and present the expressed antigen through the MHC class I restricted processing pathway. Dendritic cells were prepared by depleting bone marrow cells of lymphocytes and culturing overnight in RPMI 1640 supplemented with 10% FCS, L-glutamine, antibiotics and 2-ME in 24 well plates at $10^6$ cells/well. Cells were repleted on day 1 at $2.5 \times 10^5$ cells/well with GM-CSF ($10^3$ U/ml, Sigma, St. Louis, Mo.) and murine rIL-4 ($10^3$ U/ml, Genzyme, Cambridge, Mass.) and loosely adherent cells were harvested on day 8. By flow cytometric analysis, these dendritic cells expressed CD45, CD44, CD11b (Mac-1), CD18, CD80, cD86 and class I and class II MHC antigens. Dendritic cells were pulsed 2 hrs at 37° C. with or without OVA peptide (20 ng/ml)+$\beta$2-microglobin ($\beta$2-M, 10 μl/ml, human, Sigma) in reduced serum media (Optimen, Gibco, Grand Island, N.Y.). Cells were then washed extensively, resuspended in PBS and irradiated (2000 rad) before injection into naive mice. The indicated number of bone marrow derived dendritic APCs were cocultured with OVA-encoding particulate polynucleotides prepared as described in Example Section 7 (50 μl/ml/$10^6$ cells of 7 mg/ml particulates) using either Fe beads (closed squares) or gold beads (closed circles) as the particulate substrate or soluble OVA protein (2 mg/ml) (open squares) for 24 hrs., washed, and then the indicated number of APCs were co-cultured in microcultures with the T-cell hybridoma RF33.70 (anti-OVA+$K^b$). After 18 hrs incubation, supernatants were harvested and assayed for IL-2 using the indicator cell line HT2 (Rock, et al., 1990, *J. Immunol.* 145: 804–811).

FIG. 6 shows that immunization with APCs which had been co-incubated with particulate polynucleotide encoding OVA protects animals from challenge by OVA-expressing melanoma MO5, Groups of 5 C57B1/6 mice were immunized subcutaneously as described in FIG. 5 on one occasion and then challenged by intradermal injection of $1 \times 10^5$ MO5 tumor cells in each flank 10 days after immunization. Immunizations consisted of either: (open squares) particulate polynucleotide encoding the irrelevant antigen $\beta$-galactosidase (100 μl of 7 mg/ml particulate solution (particulate wt./vol PBS) per hind leg bilaterally; (open circles) salable pAc-neo-OVA (100 μl per hind leg containing an approximately equivalent quantity of DNA/animal); or (closed squares) $5 \times 10^4$ bone marrow derived dendritic cells/100 μl hind legs s.q. (prepared as described in Example 7). Survival was reported as the percentage of surviving animals. All experiments included 5 mice per group. Mice that became moribund were sacrificed according to animal care guidelines.

5. DETAILED DESCRIPTION OF THE INVENTION

As used herein, the term "mammalian host" includes members of the animal kingdom, including but not limited to human beings.

As used herein, the term "DNA fragment" may include any nucleotide sequence, either DNA or RNA, which contains appropriate coding region and regulatory sequences to result in target cell expression of an antigenic protein or antigenic protein fragment for cell membrane presentation via the endogenous MHC Class I pathway.

As used herein, the term "particulate polynucleotide" may refer to a particulate made from materials including but not limited to gold, iron, and synthetic plastics wherein the particle comprises a population of DNA fragments as defined in the preceding paragraph.

The present invention relates to therapeutic or prophylactic genetic immunization of a mammalian host which comprises delivery of a DNA fragment to a target cell within the mammalian host, expression of the DNA fragment within the target cell, and subsequent presentation of a recombinant antigenic peptide(s) within the target cell so as to stimulate cell-mediated immunity, humoral immunity, or both.

The present invention further relates to therapeutic or prophylactic genetic immunization of a mammalian host which comprises delivery of a DNA fragment encoding a protein or biologically active fragment thereof to a specific target cell within the mammalian host. Antigenic peptides expressed from the DNA sequence are specific to an affected cell such as a neoplastic cell or virally infected cell. Antigen specific CTL production is stimulated, thereby promoting destruction of target cells such as neoplastic cells and virally infected cells.

The present invention discloses genetic immunization methods for treatment or prevention of tumors or viral infections. Cytotoxic-T-cells are a significant component of the immune response to tumors and viral infections. Cytotoxic-T-cells kill neoplastic cells or virus-infected cells through the recognition of antigenic peptides presented by MHC class I molecules on the surface of the tumor target. These peptides are derived from tumor antigens that are synthesized by the affected cell and degraded in the cytosol. Attempts to induce tumor-specific CTL responses in vivo by immunization with killed tumor cells or component proteins have generally been unsuccessful, presumably because proteins in the extracellular fluids cannot enter the cytosol and access the MHC class I presentation pathway.

A specific embodiment of the present invention relates to genetic immunization with particles containing the DNA fragment expressing the protein of interest. Such particles containing a DNA fragment are referred to throughout this specification as 'particulate polynucleotides'. In vivo cell delivery is best accomplished by administering the DNA fragment or protein of interest in particulate form, such as coated beads or gold particles. The protein or biologically active fragment is expressed subsequent to cytosolic delivery within the target cell. The expressed protein or protein fragment specific to the affected cell provides a substrate for generating an antigenic peptide(s) for presentation to T-lymphocytes via the endogenous MHC class I pathway. Appropriate presentation of the antigenic peptide or peptides of interest through the MHC class I pathway stimulate CTL production and in turn promote destruction of the affected cell.

The present invention is based on the premise that a DNA fragment expressing a tumor rejection antigen (TRA) or viral antigen or active fragment thereof may be targeted to a specific cell so as to promote the cascade of events culminating in CTL-mediated protective tumor immunity. To this end, the present invention discloses induction of CTL-mediated immunity by transfecting a target host cell with a DNA construct in particulate form which encodes an antigenic protein. The immunizing protein is produced intracellularly and hence has access to the MHC class I restricted presentation pathway. Naturally processed epitopes result, and the transfected cells may produce the immunizing protein for several days, potentially facilitating more intense immunogenic stimulation.

In a specific embodiment of the present invention a mammalian host is immunized with a particulate polynucleotide by a microprojectile bombardment device such that the particulate polynucleotide enters the cytoplasm of at least an appropriate number of host cells, preferably including but not necessarily limited to APCs, in the path of the projectiles as a direct result of non-specific projectile bombardment. When the skin is bombarded, APCs of the skin which may be bombarded include, but are not limited to epidermal Langerhans cells, keratinocytes, or dermal dendritic cells. When the lymphoid tissue is bombarded, APCs of the lymphoid tissue which may be bombarded include, but are not limited to resident dendritic cells, macrophages, stromal cells, T-lymphocytes, or β-lymphocytes. The transgenic polynucleotide is expressed at biologically effective levels such that antigenic peptide fragments are processed and presented through the endogenous MHC class I pathway and displayed on the membrane surface of the APC cells. Endogenous APC cell membrane presentation of antigen promotes the induction of antigen-specific CTLs either at the site of bombardment, or after trafficking of bombarded cells to the lymphoid tissue. Induced antigen-specific CTLs in turn circulate throughout the mammalian host, preferably a human host, to destroy neoplastic cells or virally infected cells.

A mammalian host may be immunized with a particulate polynucleotide by a biolistic (biobalistic) delivery procedure such that the particulate polynucleotide specifically enters host cells, including APCs, through the phagosome-to-cytosol pathway. Particulate polynucleotides enter host cells through the phagosome-to-cytosol pathway either at the bombarded site (skin or lymphoid tissue) or after trafficking to the lymphoid tissue. Thus, particulate polynucleotides may enter the lymphoid tissue either by direct trafficking of the particulates to the lymphoid tissue with subsequent uptake by cells in the lymphoid tissue, or by trafficking of host cells which have taken-up particulate polynucleotides to the lymphoid tissue. Subsequent to uptake by host cells, the transgenic polynucleotide is expressed at biologically effective levels such that antigenic peptide fragments are processed and presented through the endogenous MHC class I pathway and displayed on the membrane surface of the host APCs. Endogenous APC cell membrane presentation of antigen promotes the induction of antigen-specific CTLs either at the site of bombardment, or in the lymphoid tissue. Induced antigen-specific CTLs in turn circulate throughout the mammalian host, preferably a human host, to destroy neoplastic cells or virally infected cells.

In another embodiment of the present invention a mammalian host is immunized with a particulate polynucleotide by direct injection, including but not limited to subcutaneous injection, epidermal injection, dermal injection, lymphatic injection and intra venous injection. The particulate polynucleotide enters host cells and is expressed at biologically effective levels such that antigenic peptide fragments are presented to the endogenous MHC class I pathway and displayed on the membrane surface of the host cell. Endogenous target cell membrane presentation promotes the induction of antigen-specific CTLs, which in turn circulate throughout the mammalian host, preferably a human host, to destroy neoplastic cells or virally infected cells.

A mammalian host may be immunized with a particulate polynucleotide such that the particulate polynucleotide specifically enters host cells, including APCs, through the phagosome-to-cytosol pathway. Particulate polynucleotides enter host cells through the phagosome-to-cytosol pathway either at the injection site or after trafficking to the lymphoid tissue. Thus, particulate polynucleotides may enter the lymphoid tissue either by direct trafficking of the particulates to the lymphoid tissue with subsequent uptake by cells in the lymphoid tissue, or by trafficking of host cells which have taken-up particulate polynucleotides to the lymphoid tissue. Subsequent to uptake by host cells, the transgenic polynucleotide is expressed at biologically effective levels such that antigenic peptide fragments are processed and presented through the endogenous MHC class I pathway and displayed on the membrane surface of the host APCs. Endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy neoplastic cells or virally infected cells.

In another specific embodiment of the present invention a mammalian host is immunized with a particulate polynucleotide by direct injection, including but not limited to subcutaneous injection, epidermal injection, dermal injection, lymphatic injection and intra venous injection. The composition of the particulate polynucleotide is designed to include specific molecules which preferentially target APC phagocytic pathways (including, but not limited to, the mannose-receptor mediated pathway, or Fc-receptor mediated pathway) or facilitate cytosolic access of the particulate (including, but not limited to endosomal membrane fusion proteins such as the viral HA protein or the listerolysin protein). Particulate polynucleotides enter host cells through the phagosome-to-cytosol pathway either at the injection site or after trafficking to the lymphoid tissue. Thus, particulate polynucleotides may enter the lymphoid tissue either by direct trafficking of the particulates to the lymphoid tissue with subsequent uptake by cells in the lymphoid tissue, or by trafficking of host cells which have taken-up particulate polynucleotides to the lymphoid tissue. Subsequent to uptake by host cells, the transgenic polynucleotide is expressed at biologically effective levels such that antigenic peptide fragments are processed and presented through the endogenous MHC class I pathway and displayed on the membrane surface of the host APCs. Endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy neoplastic cells or virally infected cells.

The present invention is exemplified on several fronts using a murine melanoma model described in detail in Example Section 6. Briefly, the primary limitation in studying antigen specific tumor immunity in a murine model is the lack of a defined tumor antigen recognized by MHC class I restricted CTLs. Since TRAs are not fundamentally different from any other protein synthesized by the cell, except that the host is not tolerant to them, a foreign protein synthesized by a tumor should function as a tumor antigen. Tumor immunization methods of the present invention are exemplified with a murine tumor model with a defined, endogenously synthesized TRA by transfecting the ovalbumin (OVA) gene into the C57B1/6 derived melanoma B16. This system is attractive for several reasons: (1) the B16 melanoma is an extensively studied murine tumor, (2) in vivo growth characteristics and metastasis of this tumor line are well characterized, and (3) ovalbumin has a well defined structure. The intracellular processing and presentation of OVA in the C57B1/6 mouse is known. In particular the structure of the processed peptide, presented in association with MHC class I $K^b$, is known. Assays for the functional expression of ovalbumin peptide SIINFEKL (SEQ ID NO: 1) in association with $H2-K^b$ using the T-T hybridoma 33.70.Al anti-OVA-$K^b$ are also known (Kovacovics-Bankowski, et al., 1993, *Proc. Natl, Acad. Sci. USA.* 90: 4942–4946). Techniques to evaluate in vivo induction of OVA specific CTLs in this system are also well described (Moore, et al., 1988, Cell 54: 777–785).

One embodiment of the present invention is immunization with particulate polynucleotide of interest using a biolistic (biobalistic) device. Specifically, a mammalian host is immunized with a particulate polynucleotide by a biolistic (biobalistic) procedure such that the particulate polynucleotide delivery prompts a series of biological events within the transfected cells so as to elicit protective immunity to lethal tumor challenge. The present invention is exemplified severalfold by cutaneous antigen delivery using a biolistic (biobalistic) device. First, introduction of particulate polynucleotides encoding the foreign protein β-Gal results in the expression of β-Gal protein in both the epidermis and in the draining lymph nodes. Second, OVA immunization results in the induction of OVA-specific CTLs. Third, using the OVA-B16 model, it is shown that OVA-immunized animals are protected from tumor challenge by an OVA expressing tumor, and that this protection is antigen specific and dependent on CTLs. Furthermore, the mechanism of this protection goes beyond a generalized cutaneous delivery of particulate polynucleotides via a biolistic (biobalistic) device. Instead, specific targeting to phagocytic APCs and/or antigen expression in the lymphoid tissue is central to inducing antigen-specific CTLs from precursors. It is therefore a preferred embodiment of the present invention that the target cell be a phagocytic APC, specifically an APC which is localized within, or can traffic to, the lymphoid tissue.

In another embodiment of the present invention a mammalian host is immunized with a particulate polynucleotide by direct injection, including but not limited to subcutaneous injection, epidermal injection, dermal injection, lymphatic injection and intra venous injection. The transgenic polynucleotide is expressed at biologically effective levels such that antigenic peptide fragments are processed and presented through the endogenous MHC class I pathway, and displayed on the membrane surface of the target cells. Endogenous APC cell membrane presentation promotes the induction of antigen-specific CTLs, which in turn circulate throughout the mammalian host, preferably a human host, to destroy neoplastic cells or virally infected cells.

In a preferred embodiment of the present invention the target cell of a mammalian host immunized with a particulate polynucleotide by direct injection is a phagocytic APC. The transgenic polynucleotide is expressed at biologically effective levels such that antigenic peptide fragments are presented to the endogenous MHC class I pathway and displayed on the membrane surface of the APC cell. APC cell membrane presentation promotes the induction of antigen specific CTLs, which in turn circulate throughout the mammalian host, preferably a human host, to destroy neoplastic cells or virally infected cells.

In a preferred embodiment the particulate polynucleotide is delivered to a human host by subcutaneous injection. The present invention discloses that direct injection of the particulate polynucleotide complex results in targeted delivery to phagocytic APCs and gene expression in the lymphoid tissue. It is this targeted delivery to phagocytic APCs and/or gene expression in the lymphoid tissue via subcutaneous administration which results in superior induction of antigen-specific CTLs from naive precursors.

Therefore, central to the present invention are DNA fragments encoding a protein or biologically active fragment thereof that enter and are expressed by APCs. The antigen of interest is expressed within the APC cytoplasm and enters the MHC class I pathway, allowing the APCs to promote induction of antigen-specific CTLs. The data presented in this disclosure supports the novel premise that the most effective manner in which to induce such antigen-specific CTLs is by direct transfer of genetic material to the APCs in the lymphoid tissue or APCs capable of trafficking to the lymphoid tissue.

In another embodiment of the present invention a mammalian host is immunized by injection, including but not limited to subcutaneous injection, epidermal injection, dermal injection, lymphatic injection and intra venous injection, with syngeneic APCs that have been antigen loaded in vitro with particulate polynucleotide. Specifically, a mammalian host is immunized with particulate polynucleotide transfected APCs, such that the particulate polynucleotide enters APCs in vitro and the APCs are injected into the host. Subsequent to entry into APCs, the transgenic polynucleotide is expressed at biologically effective levels such that antigenic peptide fragments are processed and presented through the endogenous MHC class I pathway and displayed on the membrane surface of the APCs. After injection of such APCs, endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy cells or virally infected cells.

In another specific embodiment of the present invention a mammalian host is immunized by injection, including but not limited to subcutaneous injection, epidermal injection, dermal injection, lymphatic injection and intra venous injection, with syngeneic APCs that have been antigen loaded in vitro by co-incubation with particulate polynucleotide. Specifically, syngeneic APCs are transfected in vitro by co-incubation with particulate polynucleotides such that the particulate polynucleotide enters the APCs through a phagosome-to-cytosol pathway. A mammalian host is immunized with particulate polynucleotide transfected APCs, such that the particulate polynucleotide specifically enters APCs through the phagosome-to-cytosol pathway and the APCs are then injected into the host. Subsequent to uptake by APCs the transgenic polynucleotide is expressed at biologically effective levels such that antigenic peptide fragments are processed and presented throughout the endogenous MHC class pathway and displaced on the membrane surface of the APCs. After injection of such APCs, endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy neoplastic cells or virally infected cells.

In another specific embodiment of the present invention a mammalian host is immunized by injection, including but not limited to subcutaneous injection, epidermal injection, dermal injection, lymphatic injection and intra venous injection, with syngeneic APCs that have been antigen loaded in vitro particulate polynucleotide. Specifically, syngeneic APCs are transferred in vitro with microprojectile bombardment of APCs with particulate polynucleotides. Subsequent to projectile bombardment into APCs, the transgenic polynucleotide is expressed at biologically effective levels such that antigenic peptide fragments are processed and presented through the endogenous MHC class I pathway and displaced on the membrane surface of the APCs. After injection of such APCs, endogenous APC cell membrane presentation of antigen promotes the induction of antigen-specific CTLs either at the site of injection, or in the lymphoid tissue. Induced antigen-specific CTLs in turn circulate throughout the mammalian host, preferably a human host, to destroy neoplastic cells or virally infected cells.

In another embodiment of the present invention a mammalian host is immunized by injection, including but not limited to subcutaneous injection, epidermal injection, dermal injection, lymphatic injection and intra venous injection, with syngeneic APCs that have been transfected in vitro with particulate polynucleotide. Specifically, a mammalian host is immunized with particulate polynucleotide transfected APCs, such that the particulate polynucleotide enters APCs in vitro and the APCs are injected into the host. Particulate polynucleotides enter APCs in vitro by either microprojectile bombardment or the phagosome-to-cytosol pathway. APCs are transfected in vitro with antigen encoding polynucleotides and/or polynucleotides encoding a molecule or molecules which increase the efficiency of the antigen presenting function of the APC, such as, but not limited to, cytokine molecules such as IL-12, IL-2, and/or IL-4 and/or costimulatory molecules such as CD80 and/or CD86. Subsequent to entry into APCs, the transgenic antigen encoding polynucleotides is expressed at biologically effective levels such that antigenic peptide fragments are processed and presented through the endogenous MHC class I pathway and displayed on the membrane surface of the APCs. After injection of such APCs, endogenous APC cell membrane presentation of antigen promotes the induction of antigen-specific CTLs either at the site of injection or in the lymphoid tissue. Induced antigen-specific CTLs in turn circulate throughout the mammalian host, preferably a human host, to destroy neoplastic cells or virally infected cells. Subsequent to entry into APCs, the transgenic cytokine and/or costimulatory encoding polynucleotide is expressed at biologically effective levels such that the antigen presenting function of the APC results in the induction of antigen specific immune responses either at the site of injection, or in the lymphoid tissue.

It will be within the purview of the artisan of ordinary skill to incorporate a TRA or viral antigen of choice into the system disclosed within this specification. Examples of presently available TRAs include, but are by no means limited to, MAGE-1, MAGE-3, BAGE, GAGE-1, GAGE-2, Tyrosinase, Melan-A(MART-1), gp100(pmel17), gp75 (TRP1), CEA (carcinoembryonic antigen) as well as viral derived tumor antigens from HPV, HBV, and EBV, as well as tumor associated oncogene/tumor suppressor gene mutation encoded antigens such as P53, P16, RAS, HER2/neu, C-ABL, and polymorphic endothelial mucin antigens (as reviewed in Maeurer et. al., 1996, *Cancer Vaccines* in Clinical Immunology Principles and Practice, ed R. Rich, Mosby Publishing. Chpt. 123:1904–1918 and Van den Eynde et al., 1995, *J. Exp. Med.* 182:689–698). Examples of viral antigens include, but are by no means limited to, Influenza nucleoprotein (Donnelly et al., 1995, *Nature Med.* 1:583–587.), HIV gp120, HIV gp 160, and Hepatitis B surface antigen (as reviewed in Pardoll and Beckerleg, *Immunity,* 1995, 3:165–169).

It is known to the artisan of ordinary skill that any eukaryotic promoter and/or enhancer sequence available which is known to up-regulate expression of a transgenic DNA sequence may be used in constructing a recombinant vector for combination with the particle of choice so as to generate the particulate polynucleotide of the present invention. Such promoter fragments include but are not limited to a cytomegalovirus (CMV) promoter, a Rous Sarcoma virus (RSV) promoter, a Murine Leukemia Virus (MLV) promoter, a β-actin promoter, as well as any cell-specific promoter or enhancer sequence known to be active in the target cell.

To this end, a preferred embodiment of the present invention is the use of particulate bound DNA to deliver the DNA encoding a tumor or viral antigen specifically to the APCs in the lymphoid tissue, or APCs capable of trafficking to the lymphoid tissue, so as to promote MHC class I access of antigen, thus allowing APCs to stimulate induction of antigen-specific CTLs. These CTLs will then circulate throughout the host and destroy neoplastic cells or virally infected cells.

Tumor immunity based on the preferred method of utilizing subcutaneous injection to promote a specific response in lymph node APCs is exemplified in Example Section 6, Example Section 7 and Example Section 8.

The following examples are offered by way of illustration of the present invention, and not by way of limitation.

6. EXAMPLE

OVA/B16 Genetic Murine Tumor Model

The OVA/B16 murine model was used to generate the data disclosed in Example Section 7 and 8 which exemplify the claimed invention. The OVA/B16 murine system is attractive for several reasons: (1) the B16 melanoma is an extensively studied murine tumor, (2) in vivo growth characteristics and metastasis of this tumor line are well characterized, and (3) ovalbumin has a well defined structure. The intracellular processing and presentation of OVA in the C57Bl/6 mouse is known. In particular the structure of the processed peptide, presented in association with MHC class I Kb, is known. Assays for the functional expression of ovalbumin peptide SIINFEKL (SEQ ID NO: 1) in association with H2-Kb using the T-T hybridoma 33.70.Al anti-OVA-Kb are also known (Kovacovics-Bankowski, et al., 1993, *Proc. Natl. Acad. Sci. USA*. 90: 4942–4946). Techniques to evaluate in vivo induction of OVA specific CTLs in this system are also well described (Moore, et al., 1988, *Cell* 54: 777–785).

Mice and Cell Lines. Female C57BL/6 mice, 5–8 weeks old were purchased from the Jackson Laboratories, Bar Harbor, Me. EL4 is a C57BL/6 T-lymphoma, and EG7 is a chicken egg ovalbumin (OVA)-transfected subclone of EL4 (Moore, et al. 1988, *Cell* 54: 777–785). The C57BL/6 derived murine melanoma B16 (Fidler, et al., 1976, *Cancer Res.* 36: 3160–3165) was obtained from American Tissue Type Collection (ATCC). MO4 was constructed by transfection of B16 with the pAc-Nco-OVA plasmid as described. (Falo, et al, 1995, *Nature Med.* 1: 649–653, Moore, et al. 1988, *Cell* 54: 777–785) Monoclonal antibodies were prepared from the hybridomas GK1.5 (anti-CD4, ATCC TIB-207), 2.43 (anti-CD8 antibodies was raised in Balb/c nu/nu mice by i.p. injection of GKfl.5 cells ($3 \times 10^6$) and IFA (0.5 ml/mouse).

Figure 1:
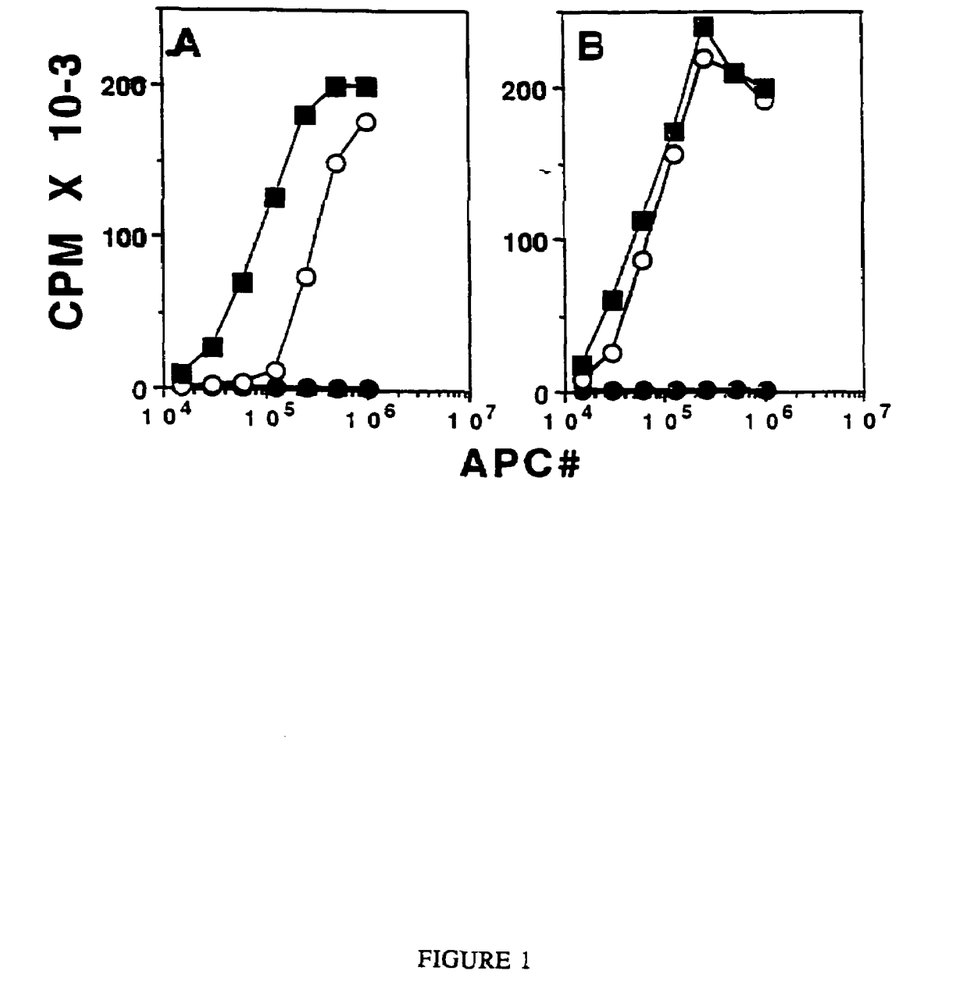
Figure 2:
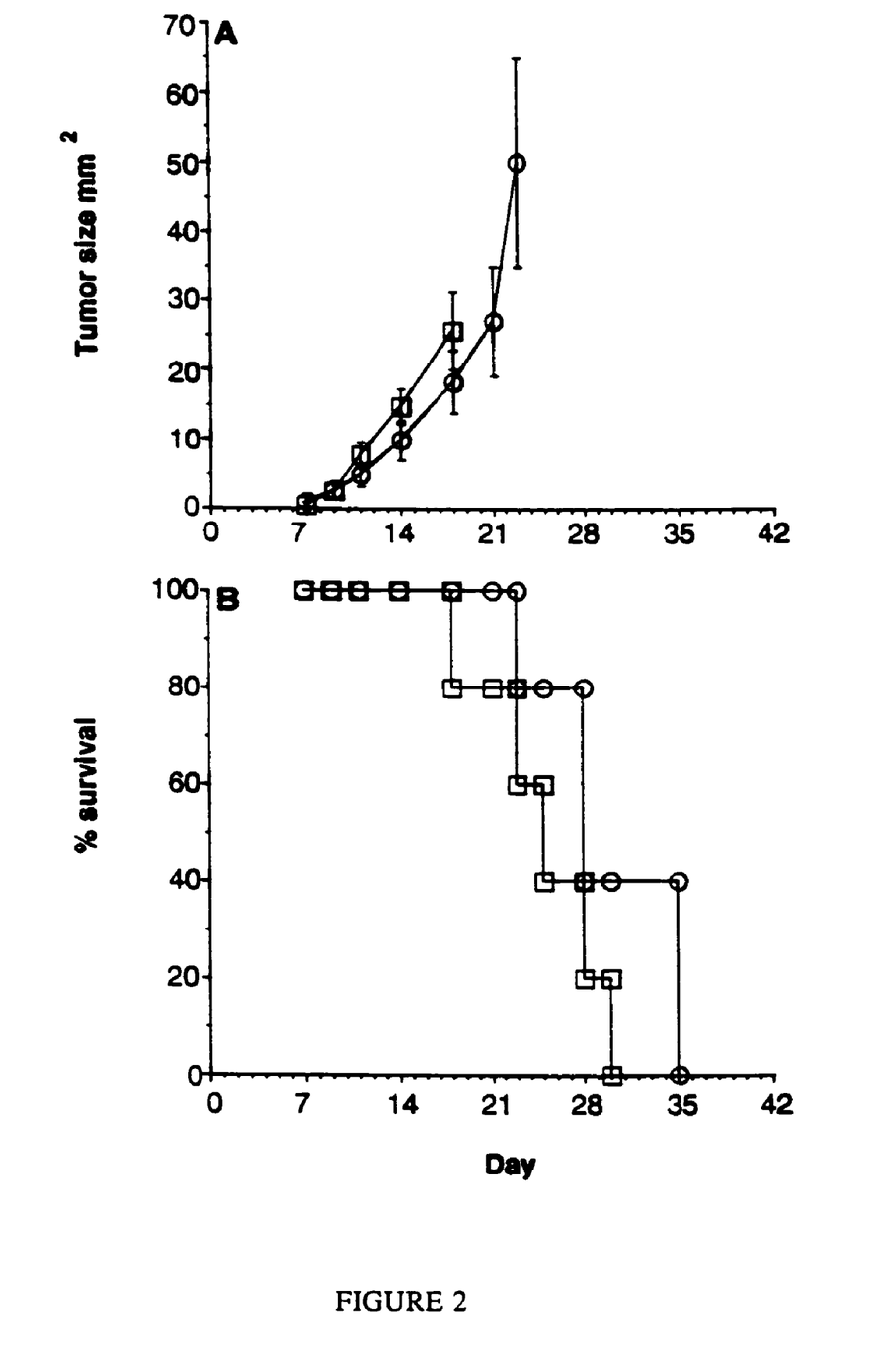
FIG. 2 shows that OVA expression by the B16 derived melanoma MO4 does not significantly effect in vivo tumor growth or host survival following tumor challenge. Mice were challenged with MO4 (circles) or B16 (squares) ($5 \times 10^4$/mouse, i.d., bilateral, mid-flanks). Tumor size (FIG. 2A) was assessed 3×/week and is reported as the average tumor area in square millimeters until the first death occurred in each group. Survival (FIG. 2B) is recorded as the percentage of surviving animals. All experiments included 5 mice/group and were repeated at least three times. Mice becoming moribund were sacrificed.

After OVA transfection of the B16 melanoma, and selection, the transfected B16 melanoma subclone, MO4 was isolated. The parent melanoma B16, and the OVA transfectant express similar levels of functional Kb on the cell surface as measured by presentation of OVA peptide SIINFEKL (SEQ ID NO: 1) to RF33.70 (FIG. 1). In contrast, MO4, but not B16, is capable of hybridoma stimulation in the absence of exogenously added peptide (FIG. 1). This demonstrates endogenous production, processing, and presentation of the transfected antigen. Importantly, endogenous expression of OVA by MO4 did not significantly alter in vivo immunogenicity of the tumor (FIG. 2). Tumor growth (FIG. 2A) of B16 and MO4 is comparable in naive mice, as is host survival (FIG. 2B).

7. EXAMPLE

Genetic Immunization Via Biolistic (Biobalistic) Administration

Localization of Foreign Protein Expression—Tissue specimens (skin or draining lymph nodes) were harvested 24 or 48 hours after immunization, washed in PBS and fixed in 2% formaldehyde—0.2% glutaraldehyde in PBS for 30 min. at 4° C. Fixed specimens were washed extensively with PBS and then incubated in X-gal staining solution (1 mg/ml X-gal, 5 mM potassium ferricyanide, 5 mM ferrocyanide, 2 mM $MgCl_2$ in PBS) for 18 hrs at 37° C. Stained tissue was paraffin sectioned and counterstained with 0.1% nuclear fast red.

Genetic Immunization—DNA coated gold particles were prepared by combining 50 mg of 0.95 μm gold beads and 100 μl of 0.1 M spermidine and sonicating for 5 seconds. 132 μg of plasmid DNA and 200 μl of $CaCl_2$ were added sequentially while vortexing. This mixture was allowed to precipitate at room temperature for 5–10 minutes. The bead preparation was then centrifuged (10,000 rpm for 30 seconds) and washed 3 times in cold ethanol before re-suspension in 7 ml of ethanol to give a final concentration of 7 mg gold/ml. The solution was then loaded into Tefzel® tubing (Agracetus) and allowed to settle for 5 minutes. The ethanol was removed and the beads were attached to the sides of the tubing by rotation at 20 rpm for 30 seconds and $N_2$ dried. The dry tubing lined with beads was then cut into 0.5 inch sections and stored for use with desiccant in parafilm sealed vials. Animals were vaccinated by delivery of 2 shots (each shot consisted of 0.5 mg gold beads=0.5 inch of tubing) to the shaved abdominal region using the Accell Gene Delivery Device at a discharge pressure of 300 psi. Animals were immunized with either the pAc-Neo-OVA plasmid (Moore, et al., 1988, *Cell* 54: 777–785) or the pIEglacZ plasmid (provided by Nadia Jouroud) which contains the lacZ gene under the control of the CMV promoter. For experiments involving subcutaneous injection of particulate polynucleotides (FIG. 5) DNA coated beads were prepared as above and an equivalent quantity of DNA was injected. For some animals (FIG. 5), an excess quantity of free plasmid DNA was subcutaneously injected. Subcutaneous injections were administered in 100 μl volume of PBS in the mid-flanks, bilaterally. For in vitro transfection of APCs (FIG. 4), DNA beads were identically prepared using an equivalent weight of Biomag iron oxide beads or gold beads as a particulate substrate.

For experiments involving subcutaneous injection of particulate polynucleotides (FIGS. 5 and 6) DNA coated beads were prepared as above and an equivalent quantity of DNA was injected, or the quantity specified in the figure descriptions. For some animals (FIGS. 5 and 6), an excess quantity of free plasmid DNA was subcutaneously injected. Subcutaneous injections were administered in 100 μl volume of PBS in the hind legs, bilaterally.

For in vitro transfection of APCs (FIGS. 4 and 6), DNA beads were identically prepared as described above using an equivalent weight of Biomag iron oxide beads (Fe beads) or gold beads as particulate substrate. Dendritic APCs were obtained from bone marrow as described in the Brief Description of the Drawings except that IL-4 was not used in tissue culture media with 25 μl of 7 mg/ml particulate polynucleotide solution (particulate wt/vol. PBS) for 18 hrs at 37° C. Antigen-pulsed dendritic cells were prepared and injected as described in the Brief Description of the Drawings. Briefly, dendritic cells were prepared by depleting bone marrow cells of lymphocytes and culturing overnight in RPMI 1640 supplemented with 10% FCS, L-glutamine, antibiotics and 2-ME in 24 well plates at $10^6$ cells/well. Cells were repleted on day 1 at $2.5 \times 10^5$ cells/well with GM-CSF ($10^3$ U/ml, Sigma, St. Louis, Mo.) and murine rIL-4 ($10^3$ U/ml, Genzyme, Cambridge, Mass.) and loosely adherent cells were harvested on day 8. By flow cytometric analysis, these dendritic cells expressed CD45, CD44, CD11b (Mac-1), CD18, CD80, cD86 and class I and class II MHC antigens. Dendritic cells were pulsed 2 hrs at 37° C. with or without OVA peptide (20 ng/ml)+β2-microglobin (β2-M, 10 µl/ml, human, Sigma) in reduced serum media (Optimen, Gibco, Grand Island, N.Y.). Cells were then washed extensively, resuspended in PBS and irradiated (2000 rad) before injection into naive mice.

Cytotoxicity Assays—Splenocytes from immunized animals were restimulated with minor modifications of previously described protocols. (Falo, et al., 1995, *Nature Med.* 1: 649–653). Briefly, 1 week after immunization splenocytes ($30 \times 10^6$) were restimulated by coculture with irradiated (20,000 rad) EG7 cells ($10 \times 10^6$). Effector cells were harvested five days later and cultured with $2 \times 10^4$ $^{51}$Cr labeled targets in round bottom microwells (200 µl) at the indicated effector target cell ratio. In some cases the effector cells were depleted of T-cell subsets using mAB plus complement before assay as described. (Rock, et al., 1993, *J. Immunol.* 150: 1244–1251). After 4 hours at 37° C., 100 µl of supernatant from triplicate microcultures was collected and counted and the percentage of specific release was calculated as described. (Falo, et al., 1995, *Nature Med.* 1: 649–653). Results are reported as the mean of triplicate cultures. The SEM of triplicate cultures was always less than 15% of the mean.

Protection Assays—C57BL/6 mice were immunized as described with the indicated antigen gene construct. Animals were challenged with tumors and evaluated for tumor survival as described. Briefly, seven days after the final immunization (day 0), OVA-immunized or lacZ-immunized animals were challenged by intradermal injection in the midflanks bilaterally with melanoma cells ($2 \times 10^4$) at 2 times the dose lethal to 50% of the animals tested ($LD_{50}$) or the number of tumor cells indicated in section 4. Survival is recorded as the percentage of surviving animals. Melanoma cells for injection were washed three times in PBS. Injected cells were greater than 95% viable by trypan blue exclusion. All experiments included 5 mice per group and were repeated at least three times. Mice which became moribund were sacrificed according to animal care guidelines of the University of Pittsburgh Medical Center. In some experiments, animals were depleted of $CD8^+$ cells. This was accomplished by i.p. injection of CD8 mAb (2.43) 7 and 9 days after immunization as described, followed by tumor challenge on day 10 (Falo, et al., 1995, *Nature Med.* 1: 649–653).

Figure 3:
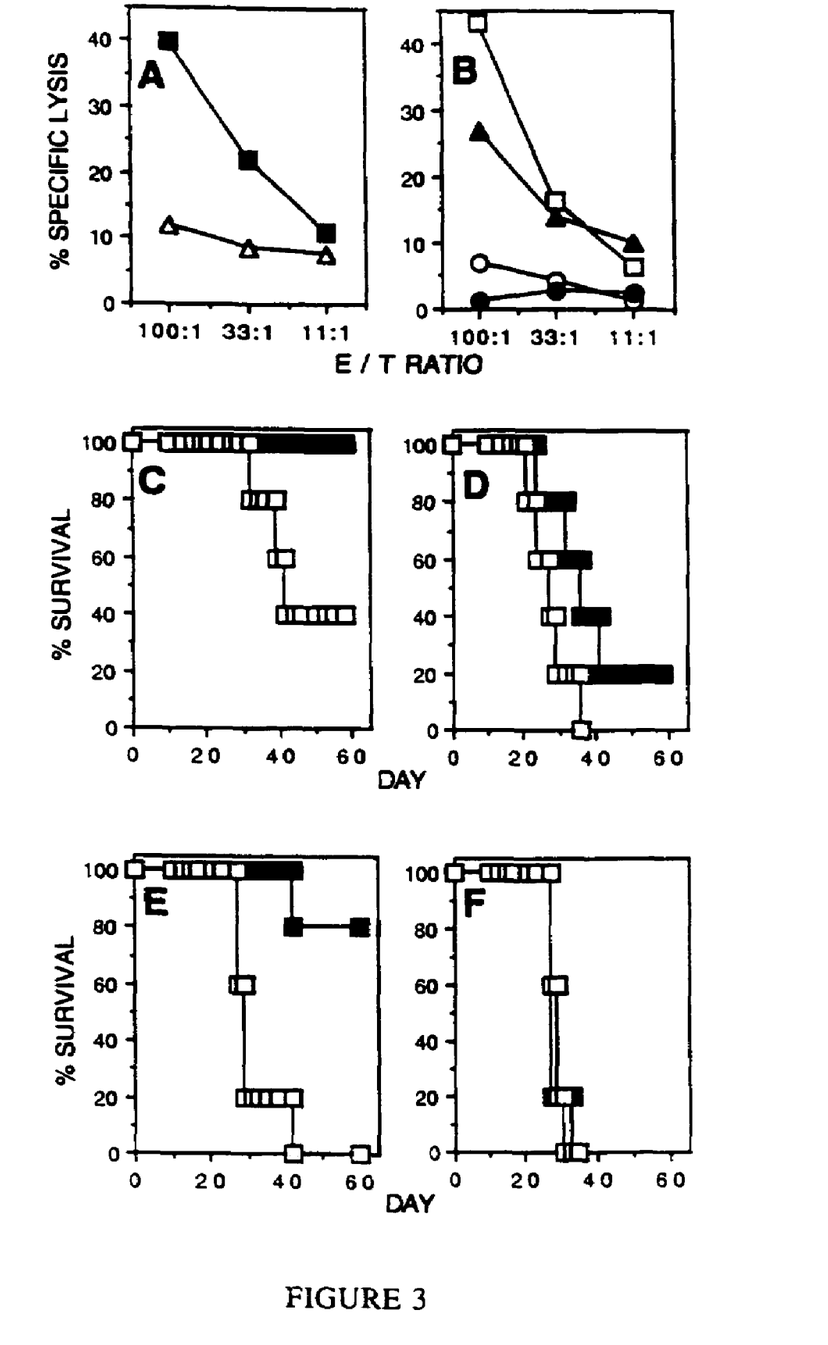

The capacity of biolistic (biobalistic) immunization to induce antigen specific CTLs was evaluated. Naive C57B1/6 mice were immunized with a total of at most 2.64 µg of OVA encoding DNA delivered to the abdominal skin with 2 overlapping pulses, and identically boosted 7 days later. In vitro restimulated spleen cells from these mice lysed the syngeneic OVA-expressing murine thymoma EG7, but not the untransfected parent tumor EL4 (FIG. 3A). Thus, target cell lysis was antigen specific, depending on expression of OVA by the tumor target. Depletion of T-Cell subsets from the effector populations using mABs demonstrated that lysis depended on Thy $1^+$, $CD8^+$ subsets characteristic of MHC class I-restricted CTL effector cells (FIG. 3B).

Groups of mice that were immunized and boosted as described above were challenged 7 days later by i.d. injection of the MO4 melanoma at a distant site to determine the ability of biolistic (biobalistic) immunization to induce protective tumor immunity. OVA-immunized mice were protected from lethal tumor challenge, while tumors in control mice (immunized similarly, but with the lacZ reporter gene) grew progressively and were lethal in 60% of the animals by day 40 (FIG. 3C). OVA-immunized mice were not protected from challenge with the untransfected parent melanoma B16 (FIG. 3D), indicating that protective immunity was antigen specific, depending on OVA expression by the tumor target. We evaluated the contribution of $CD8^+$ effector cells to this protective tumor immunity by depleting groups of immunized or control (lacZ immunized) animals of $CD8^+$ effector cells through repeated i.p. injection of anti-CD8mAB before tumor challenge. (Falo, et al., 1995, *Nature Med.* 1: 649–653). While OVA-immunized animals were protected from MO4 challenge, survival in immunized, CD8+ T-cell depleted animals was similar to that observed in control animals, with or without T-cell depletion (FIGS. 3E–F). Therefore, $CD8^+$ T-cells are essential for the protective tumor immunity induced by genetic immunization in this model.

Additional evidence supporting the proposed mechanism of tumor immunity includes the demonstration of β-galactosidase expression in the epidermis after biolistic (biobalistic) delivery of the lacZ construct, and, interestingly, discrete areas of specific expression within the draining lymph nodes. As these nodes were distant from the immunization site, it is unlikely that lymph node expression was a result of direct physical bombardment. There was a predominance of gold particles in the epidermis and dermis of immunized skin (unstained) 24 hrs after DNA delivery and lacZ expression within epidermal keratinocytes at 48 hrs. There are also discrete areas of specific staining within the draining lymph nodes. Identically treated specimens from mice immunized with irrelevant DNA did not show lacZ expression. This observation prompted further analysis which is disclosed in Example Section 8.

8. EXAMPLE

Genetic Immunization by Subcutaneous Administration

The materials and methods for inducing tumor immunity by subcutaneous administration of a particulate polynucleotide are as described throughout Example Section 6 and Example Section 7.

This data demonstrates an ability to specifically target phagocytic APCs in the lymphoid tissue, or APCs capable of trafficking to the lymphoid tissue, by subcutaneous injection of particulate polynucleotides in vivo.

Figure 5:
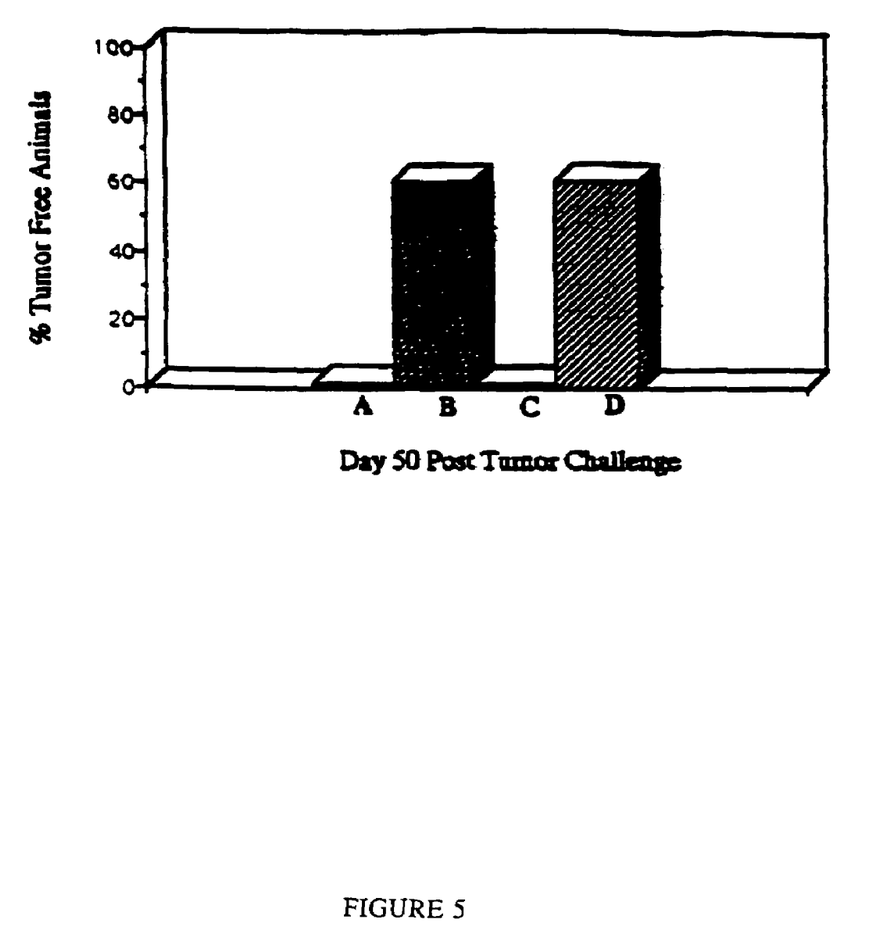
FIG. 5 shows a comparison of particulate polynucleotide immunization administered by biolistic (biobalistic) or subcutaneous injection. Groups of 5 C57B1/6 mice were immunized, boosted on day 7, and then challenged by intradermal injection of $5 \times 10^5$ MO5 tumor cells in each flank 7 days after boosting. Immunizations consisted of: (A) $\beta$-Gal encoding particulate polynucleotides prepared and delivered by biolistic (biobalistic) administration as described in Example Section 7; (B) OVA encoding particulate polynucleotides prepared and delivered by biolistic (biobalistic) administration as described in Example Section 7; (C) an excess quantity of OVA encoding polynucleotide without particulates delivered by subcutaneous injection; or, (D) an equivalent amount of OVA encoding particulate polynucleotides prepared as in Example Section 7 but administered by subcutaneous injection. Data is presented as % of animals tumor free in each group 50 days after tumor challenge.

Protection from tumor challenge was equivalent within groups of mice immunized with particulate polynucleotides comprising pAc-Neo-OVA either by direct subcutaneous injection or by biolistic (biobalistic) administration (FIG. 5). Consistent with the findings in Example Section 7, immunization with a particulate polynucleotide encoding and irrelevant antigen (e.g., pIEglacZ) did not confer protection (FIG. 5). Subcutaneous injection of pAc-Neo-OVA without particulates did not confer protection from a relevant tumor challenge (FIG. 5). These data indicate that subcutaneous injection of particulate polynucleotides is at least as effective as biolistic (biobalistic) particulate delivery. Furthermore, as subcutaneous injection does not result in direct physical projectile bombardment of polynucleotide particles into the cytoplasm of individual host cells, expression likely requires active uptake of polynucleotides by host cells capable of phagocytosis/endocytosis. The observation that subcutaneous injection of pAc-Neo-OVA without particulates did not confer protection also implicates particulate delivery/phagocytosis as the mechanism of transduction. Particulate transduction by phagocytosis implies that transgene expression is preferentially targeted to cells capable of phagocytosis, including APCs.

simulators of antigen-specific CTLS and protective tumor immunity when peptide-loaded in vitro are at least similarly immunogenic which antigen-loaded by co-incubation with particulate polynucleotides.

Taken together, these results indicate that subcutaneous administration of particulate polynucleotides has the advantage of targeting delivery of antigens to phagocytic APCs, potentially increasing the efficiency of genetic immunization while reducing unwanted deleterious effects, including but not limited to tolerance induction or mutagenesis resulting from the transfection of normal, non-APC host cells.

SEQUENCE LISTING

```
<160> NUMBER OF SEQ ID NOS: 2

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
  1               5

<210> SEQ ID NO 2
<211> LENGTH: 9
<212> TYPE: PRT
<213> ORGANISM: Gallus gallus

<400> SEQUENCE: 2

Ser Ile Ile Asn Phe Glu Lys Leu Lys
  1               5
```

Figure 4:
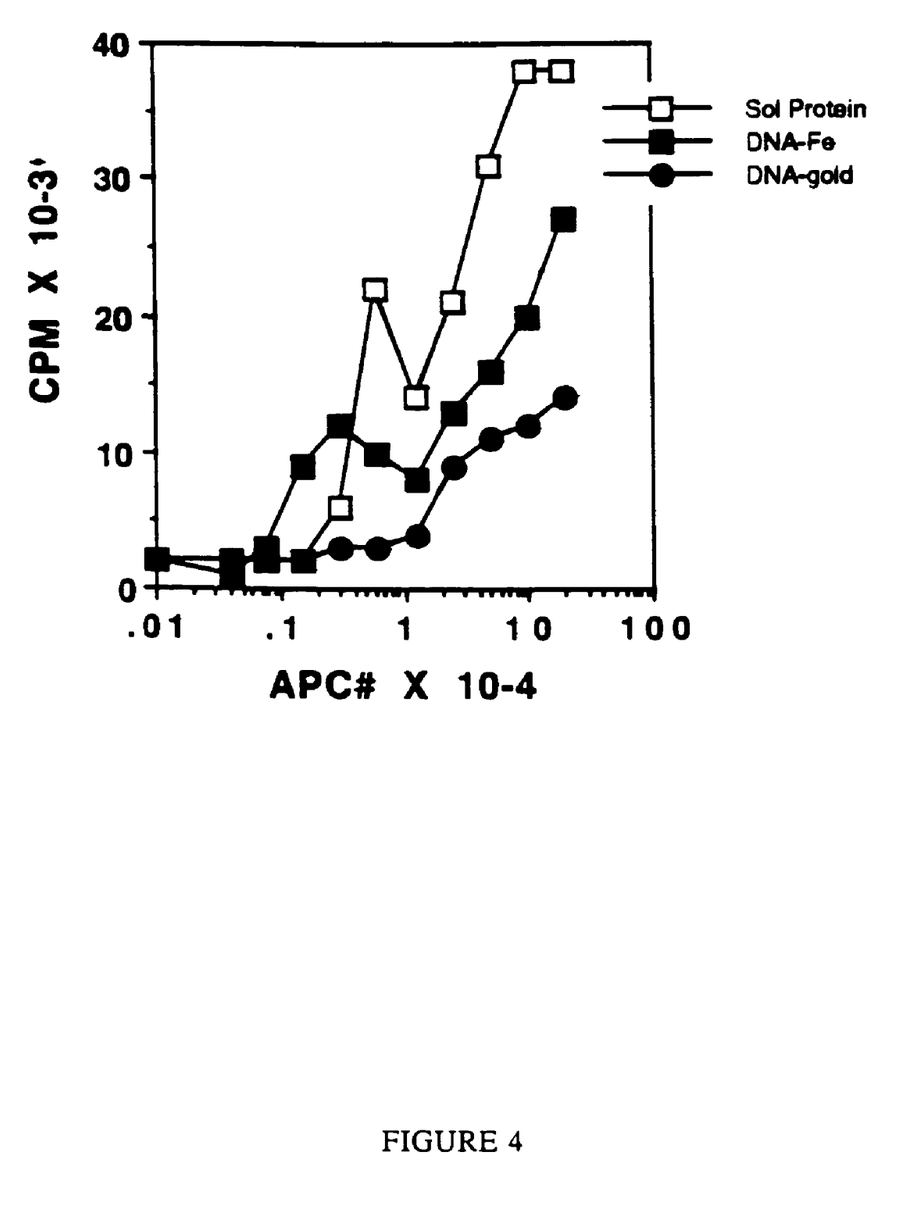

In further support of this proposed mechanism is the observation that APCs (bone marrow derived dendritic cells) co-cultured in vitro with particulate polynucleotides encoding ovalbumin (prepared as described in Example 7) (pAc-Neo-OVA) can stimulate the OVA SIINFEKL$^+$ K$^b$ (SEQ ID NO: 2) specific T cell hybridoma RF33.70 to produce IL-2 (FIG. 4). These data demonstrate that these APCs functionally express the ovalbumin gene and generate the ovalbumin peptide-K$^b$ complex. The potency of stimulation is comparable to that observed with APCs pulsed with 2 mg/ml of soluble OVA protein. Particulate polynucleotides are effective in this assay using either gold or Fe as the particulate substrate. Thus, the incubation of particulate polynucleotides with phagocytic APCs in vitro results in the endogenous production, processing, and presentation of the transfected antigen. These observations demonstrate that particulate polynucleotides can be taken up and expressed by APCs, and that the corresponding proteins can be functionally presented to induce antigen specific immune responses.

Figure 6:
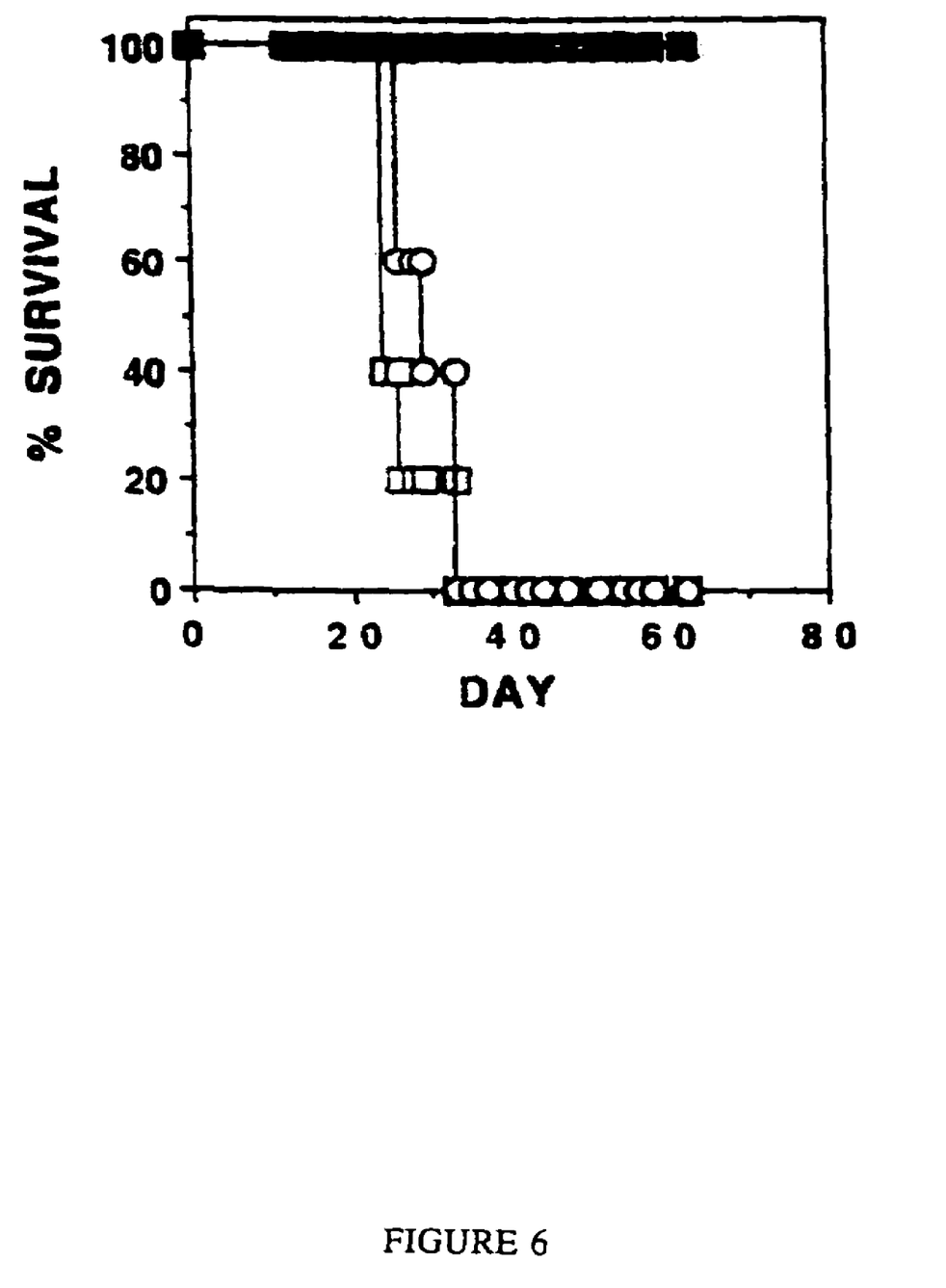

Furthermore, as shown in FIG. 6, antigen presenting cells, in this case subcutaneously injected bone marrow derived dendritic cells, which have been incubated with particulate polynucleotides encoding the antigen OVA in vitro as described above, are capable of inducing protective immunity to tumor cells expressing the antigen gene. In the example given, a one time administration of $10^5$ irradiated transfected dendritic cells/animal ($5 \times 10^4$ cells per hind leg, bilaterally) induced complete protection to tumor challenge. Thus, in vivo administered dendritic APCs, which are potent

What is claimed is:

1. An in vivo method of treating a mammalian host capable of generating an immune response, which comprises:
    (a) generating a DNA fragment which expresses an antigenic protein or antigenic protein fragment;
    (b) distributing said DNA fragment on a particle surface, resulting in a particulate polynucleotide;
    (c) inoculating said mammalian host with said particulate polynucleotide by direct injection; and,
    (d) delivering said particulate polynucleotide to the cytoplasm of an antigen presenting cell within said mammalian host, such that said expressed antigenic protein or antigenic protein fragment is presented to the membrane surface of said antigen presenting cell through the MHC class I pathway, wherein said presentation of said antigenic protein or protein fragment elicits an anti-tumor or anti-viral immune response in said host that destroys neoplastic or virally infected cells.

2. The method of claim 1 wherein said mammalian host is a human.

3. The method of claim 2 wherein direct injection is by subcutaneous injection.

4. The method of claim 3 wherein said DNA fragment expresses a tumor rejection antigen, viral antigen or antigenic protein fragment thereof.

5. The method of claim 4 wherein said antigen presenting cell resides within or migrates to the lymphoid tissue of said human host.

6. The method of claim 5 wherein said tumor rejection antigen is selected from the group consisting of MAGE-1 and MAGE 3.

7. The method of claim 5 wherein said tumor rejection antigen is Melan-A.

8. The method of claim 5 wherein said tumor rejection antigen is gp100.

9. The method of claim 5 wherein said tumor rejection antigen is p53.

10. The method of claim 5 wherein said tumor rejection antigen is CEA.

11. The method of claim 5 wherein said tumor rejection antigen is HER2/neu.

12. The method of claim 5 wherein said viral antigen is Influenza virus nucleoprotein.

13. The method of claim 5 wherein said viral antigen is Hepatitis B surface antigen.

14. The method of claim 1, wherein said direct injection is subcutaneous injection, epidermal injection, dermal injection, lymphatic injection or intravenous injection.

15. The method of claim 1, wherein said antigen presenting cell is a dendritic cell, macrophage, a stromal cell, T-lymphocyte or B-lymphocyte.

16. The method of claim 15, wherein said antigen presenting cell is a dendritic cell.

17. An ex vivo method of treating a mammalian host capable of generating an immune response, which comprises:
(a) generating a DNA fragment which expresses an antigenic protein or antigenic protein fragment;
(b) distributing said DNA fragment on a particle surface, resulting in a particulate polynucleotide;
(c) delivering said particulate polynucleotide to the cytoplasm of an antigen presenting cell of a mammalian host in vitro, such that said expressed antigenic protein or antigenic protein fragment is presented on the membrane surface of said antigen presenting cell through the MHC class I pathway; and,
(d) inoculating said mammalian host with said antigen presenting cell by direct injection, wherein presentation of said expressed antigenic protein or protein fragment on said antigen presenting cells of said hosts elicits an anti-tumor or anti-viral immune response that destroys neoplastic or virally-infected cells in said host.

18. The method of claim 17 wherein said mammalian host is a human.

19. The method of claim 18 wherein direct injection is by subcutaneous injection.

20. The method of claim 19 wherein said DNA fragment expresses a tumor rejection antigen, viral antigen or antigenic protein fragment thereof.

21. The method of claim 20 wherein said antigen presenting cells resides within or migrates to the lymphoid tissue of said human host.

22. The method of claim 21 wherein said tumor rejection antigen selected from the group consisting of MAGE-1 and MAGE 3.

23. The method of claim 21 wherein said tumor rejection antigen is Melan-A.

24. The method of claim 21 wherein said tumor rejection antigen is gp100.

25. The method of claim 21 wherein said tumor rejection antigen is p53.

26. The method of claim 21 wherein said tumor rejection antigen is CEA.

27. The method of claim 21 wherein said tumor rejection antigen is HER2/nue.

28. The method of claim 21 wherein said viral antigen is Influenza virus nucleoprotein.

29. The method of claim 21 wherein said viral antigen is Hepatitis B surface antigen.

30. The method of claim 17, wherein said direct injection is subcutaneous injection, epidermal injection, dermal injection, lymphatic injection or intravenous injection.

31. The method of claim 17, wherein said antigen presenting cell is a dendritic cell, macrophage, a stromal cell, T-lymphocyte or B-lymphocyte.

32. The method of claim 31, wherein said antigen presenting cell is a dendritic cell.

33. An ex vivo method of treating a mammalian host capable of generating an immune response, which comprises:
(a) generating a DNA fragment which expresses a molecule which enhances the antigen presentation function of an APC;
(b) distributing said DNA fragment on a particle surface, resulting in a particulate polynucleotide;
(c) delivering said particulate polynucleotide to the cytoplasm of an antigen presenting cell of a mammalian host in vitro, such that said antigen presentation enhancing protein is expressed; and,
(d) inoculating said mammalian host with said antigen presenting cell by direct injection.

34. The method of claim 33 wherein said mammalian host is a human.

35. The method of claim 34 wherein direct injection is by subcutaneous injection.

36. The method of claim 35 wherein said antigen presenting cell resides within or migrates to the lymphoid tissue of said human host.

37. The method of claim 36 wherein said DNA fragment expresses a costimulatory molecule.

38. The method of claim 37 wherein said costimulatory molecule is selected from the group consisting of CD80 and CD86.

39. The method of claim 36 wherein said DNA vector fragment expresses a cytokine molecule.

40. The method of claim 39 wherein said cytokine molecule is selected from the group consisting of IL-12, IL-4 and IL-2.

41. The method of claim 33, wherein said direct injection is subcutaneous injection, epidermal injection, dermal injection, lymphatic injection or intravenous injection.

42. The method of claim 33, wherein said antigen presenting cell is a dendritic cell, macrophage, a stromal cell, T-lymphocyte or B-lymphocyte.

43. The method of claim 42, wherein said antigen presenting cell is a dendritic cell.

44. A method for transfecting an antigen presenting cell comprising:
(a) distributing a DNA fragment which expresses an antigenic protein or fragment thereof on a particle surface, resulting in a particulate polynucleotide;
(b) delivering said particulate polynucleotide by direct injection to the cytoplasm of an antigen presenting cell, such that said expressed antigenic protein or fragment thereof is presented to the membrane surface of said antigen presenting cell, whereby presentation of said antigenic protein or protein fragment elicits an anti-tumor or anti-viral immune response in a mammalian host that destroys neoplastic or virally infected cells.

45. The method of claim 44, wherein said delivering step occurs in vivo.

46. The method of claim 44, wherein said delivering step occurs in vitro.

47. The method of claim 44, wherein said mammalian host is a human.

48. The method of claim 47, wherein said antigen presenting cell resides within or migrates to the lymphoid tissue of said human host.

49. The method of claim 44, wherein said DNA fragment expresses a tumor rejection antigen, viral antigen or antigenic protein fragment thereof.

50. The method of claim 49, wherein said tumor rejection antigen is selected from the group consisting of MAGE-1 and MAGE 3.

51. The method of claim 49, wherein said tumor rejection antigen is Melan-A.

52. The method of claim 49, wherein said tumor rejection antigen is gp100.

53. The method of claim 49, wherein said tumor rejection antigen is p53.

54. The method of claim 49, wherein said tumor rejection antigen is CEA.

55. The method of claim 49, wherein said tumor rejection antigen is HER2/neu.

56. The method of claim 49, wherein said viral antigen is Influenza virus nucleoprotein.

57. The method of claim 49, wherein said viral antigen is Hepatitis B surface antigen.

58. The method of claim 57, wherein said direct injection is subcutaneous injection.

59. The method of claim 58, wherein said antigen presenting cell resides within or migrates to the lymphoid tissue of said human host.

60. The method of claim 59, wherein said antigen presenting cell is a dendritic cell.

61. The method of claim 44, wherein said antigen presenting cell is a dendritic cell, macrophage, a stromal cell, T-lymphocyte or B-lymphocyte.

62. The method of claim 61, wherein said antigen presenting cell is a dendritic cell.

63. The method of claim 44, wherein said direct injection is subcutaneous injection, epidermal injection, dermal injection, lymphatic injection or intravenous injection.

64. The method of claim 44, wherein said antigen presenting cell is a dendritic cell, macrophage, a stromal cell, T-lymphocyte or B-lymphocyte.

65. A method of inducing a CTL immune response in a mammalian host capable of generating an immune response, comprising the step of transfecting antigen presenting cells of said host in vivo with a DNA fragment which expresses an antigenic protein or fragment thereof by direct injection, such that said antigenic protein or fragment thereof is presented to the membrane surface of said antigen presenting cell through the MHC class I pathway and tumor cells are destroyed.

66. The method of claim 65, wherein said mammalian host is a human.

67. The method of claim 66, wherein said tumor rejection antigen is selected from the group consisting of MAGE-1 and MAGE 3.

68. The method of claim 66, wherein said tumor rejection antigen is Melan-A.

69. The method of claim 66, wherein said tumor rejection antigen is gp100.

70. The method of claim 66, wherein said tumor rejection antigen is p53.

71. The method of claim 66, wherein said tumor rejection antigen is CEA.

72. The method of claim 66, wherein said tumor rejection antigen is HER2/neu.

73. The method of claim 66, wherein said viral antigen is Influenza virus nucleoprotein.

74. The method of claim 66, wherein said viral antigen is Hepatitis B surface antigen.

75. The method of claim 74, wherein said direct injection is subcutaneous injection.

76. The method of claim 65, wherein said DNA fragment expresses a tumor rejection antigen, viral antigen or antigenic protein fragment thereof.

77. The method of claim 65, wherein said direct injection is subcutaneous injection, epidermal injection, dermal injection, lymphatic injection or intravenous injection.

78. An in vivo method of generating an immune response in a mammalian host capable of generating an immune response comprising:
(a) generating a DNA fragment which expresses an antigenic protein or antigenic protein fragment;
(b) distributing said DNA fragment on a particle surface, resulting in a particulate polynucleotide;
(c) inoculating said mammalian host with said particulate polynucleotide by direct injection; and
(d) delivering said particulate polynucleotide to the cytoplasm of an antigen presenting cell within said mammalian host, such that said expressed antigenic protein or antigenic protein fragment is presented to the membrane surface of said antigen presenting cell through the MHC class I pathway, wherein said presentation of said antigenic protein or protein fragment elicits an anti-tumor or anti-viral immune response in said host.

79. An in vivo method of treating a mammalian host capable of generating an immune response comprising:
(a) generating a DNA fragment which expresses an antigenic protein or antigenic protein fragment;
(b) distributing said DNA fragment on a particle surface, resulting in a particulate polynucleotide;
(c) inoculating said mammalian host with said particulate polynucleotide by direct injection; and,
(d) delivering said particulate polynucleotide to the cytoplasm of an antigen presenting cell within said mammalian host, such that said expressed antigenic protein or antigenic protein fragment is presented to the membrane surface of said antigen presenting cell through the MHC class I pathway, wherein said presentation of said antigenic protein or protein fragment elicits an anti-tumor response in said host that destroys neoplastic cells.

* * * * *